United States Patent
Laub et al.

(10) Patent No.: US 11,471,556 B2
(45) Date of Patent: *Oct. 18, 2022

(54) FIBRINOGEN-BASED TISSUE ADHESIVE PATCH

(71) Applicant: SEALANTIUM MEDICAL LTD., Rosh HaAyin (IL)

(72) Inventors: Orgad Laub, Tel Aviv (IL); Eran Cohen, Hod Hasharon (IL); Yotam Schwartz, Petah Tiqwa (IL)

(73) Assignee: SEALANTIUM MEDICAL LTD., Rosh Haayin (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/138,166

(22) Filed: Dec. 30, 2020

(65) Prior Publication Data

US 2021/0113734 A1  Apr. 22, 2021

Related U.S. Application Data

(63) Continuation-in-part of application No. 16/699,773, filed on Dec. 2, 2019, now Pat. No. 10,905,792, (Continued)

(51) Int. Cl.
*A61L 24/04* (2006.01)
*A61K 38/36* (2006.01)
(Continued)

(52) U.S. Cl.
CPC .......... *A61L 24/043* (2013.01); *A61K 38/363* (2013.01); *A61K 38/4833* (2013.01);
(Continued)

(58) Field of Classification Search
CPC .. A61K 33/14; A61K 38/363; A61K 2300/00; A61K 38/4833; B29D 7/01;
(Continued)

(56) References Cited

U.S. PATENT DOCUMENTS 5,607,694 A  3/1997  Marx
6,056,970 A *  5/2000  Greenawalt ............. A61P 41/00
530/382
(Continued)

FOREIGN PATENT DOCUMENTS

CN  101461966 A  6/2009
EP  0334998 A2  8/1988
(Continued)

OTHER PUBLICATIONS

Bramfeldt et al. (2007). Characterization, degradation, and mechanical strength of poly(D,L-lactide-co-s-caprolactone)-poly(ethylene glycol)poly(D,L-lactide-co-s-caprolactone). J Biomed Mater Res A. Nov. 2007;83(2):503-11. doi: 10.1002/bm.a.31300.
(Continued)

*Primary Examiner* — Jianfeng Song
(74) *Attorney, Agent, or Firm* — The Roy Gross Law Firm, LLC; Roy Gross

(57) ABSTRACT

A method of production of a tissue sealing patch is disclosed. The method comprises casting a polymer film from a biocompatible polyethylene glycol-caprolactone-lactide triblock copolymer (PECALA); softening the polymer film; placing a powdered tissue sealant material on a surface of said polymer film; and, pressing said polymer film to at least partially incorporate the sealant material into said surface of said polymer film. In some embodiments of the invention, the polymer film is created by heating and evacuating a work surface; applying a solution of PECALA to said work surface; adjusting a polymer blade to a predetermined height above said work surface; spreading said solution of PECALA over said work surface with said polymer blade; and evaporating said solvent. The PECALA preferably comprises PEG-CL-LA units connected by urethane linkages,
(Continued)

PEG having a molecular weight of between 3000 and 3500 amu, and a CL:LA:PEG ratio of 34:2:1.

8 Claims, 6 Drawing Sheets

Related U.S. Application Data which is a continuation-in-part of application No. 15/769,313, filed as application No. PCT/IL2016/051090 on Oct. 6, 2016, now abandoned.

(60) Provisional application No. 62/243,158, filed on Oct. 19, 2015.

(51) Int. Cl.
*A61K 38/48* (2006.01)
*B29D 7/01* (2006.01)
*B29L 31/00* (2006.01)
*B29K 75/00* (2006.01)

(52) U.S. Cl.
CPC .......... *B29D 7/01* (2013.01); *A61L 2300/252* (2013.01); *A61L 2400/04* (2013.01); *B29K 2075/00* (2013.01); *B29K 2995/0056* (2013.01); *B29L 2031/753* (2013.01)

(58) Field of Classification Search
CPC ........ B29K 2075/00; B29K 2995/0056; B29L 2031/753; A61L 31/046; A61L 2400/04; A61L 2300/252; A61L 24/043; A61L 31/06; C08L 71/02; C08L 75/04; C08L 67/04
See application file for complete search history.

(56) References Cited

U.S. PATENT DOCUMENTS

| 2005/0042293 | A1 | 2/2005 | Jackson et al. |
| 2007/0155906 | A1* | 7/2007 | Hissink ................ A61K 47/34 525/242 |
| 2010/0168807 | A1 | 7/2010 | Burton et al. |
| 2011/0071498 | A1* | 3/2011 | Hakimimehr .......... A61K 47/02 604/509 |
| 2011/0250283 | A1 | 10/2011 | Mitra et al. |
| 2012/0070485 | A1 | 3/2012 | Soldani et al. |
| 2014/0107159 | A1 | 4/2014 | Ebersole et al. |

FOREIGN PATENT DOCUMENTS

| EP | 1093824 A2 | 10/2000 |
| JP | S5912762 | 11/1989 |
| JP | H11216391 A | 8/1998 |
| JP | 2002213228 A | 7/2002 |
| WO | 1999021908 A1 | 5/1999 |
| WO | 2008019128 A2 | 2/2008 |
| WO | 2009119845 A1 | 10/2009 |
| WO | 2014174509 A1 | 10/2014 |
| WO | 2014174609 A1 | 10/2014 |

OTHER PUBLICATIONS

Wang et al. (2015). Fabrication and characterization of a dry electrode integrated Gecko-inspired dry adhesive medical patch for long-term ECG measurement. Microsyst Technol (2015)21:1093-1100; DOI 10.1007 s00542-014-2279-1.

Kobayashi et al. Water-curable and biodegradable prepolymers. J Biomed Mater Res. Dec. 1991;25(12):1481-94. doi: 10.1002/jbm.820251206. PMID: 1794996.

Yang et al. (2013). A bio-inspired swellable microneedle adhesive for mechanical interlocking with tissue. Nat Commun 4,1702 (2013). https://doi.org/10.1038/ncomms2715.

TISSEEL—Product Informational Pamphlet (Highlights of Prescribing Information and Full Prescribing Information). Baxter Healthcare Corporation, Westlake Village, CA.

PCT International Search Report for International Application No. PCT/IL2016/051090, dated Jan. 4, 2017, 5pp.

PCT Written Opinion for International Application No. PCT/IL2016/051090, dated Jan. 4, 2017, 7pp.

PCT International Preliminary Report on Patentability for International Application No. PCT/IL2016/051090, completed Sep. 9, 2017, 23pp.

* cited by examiner

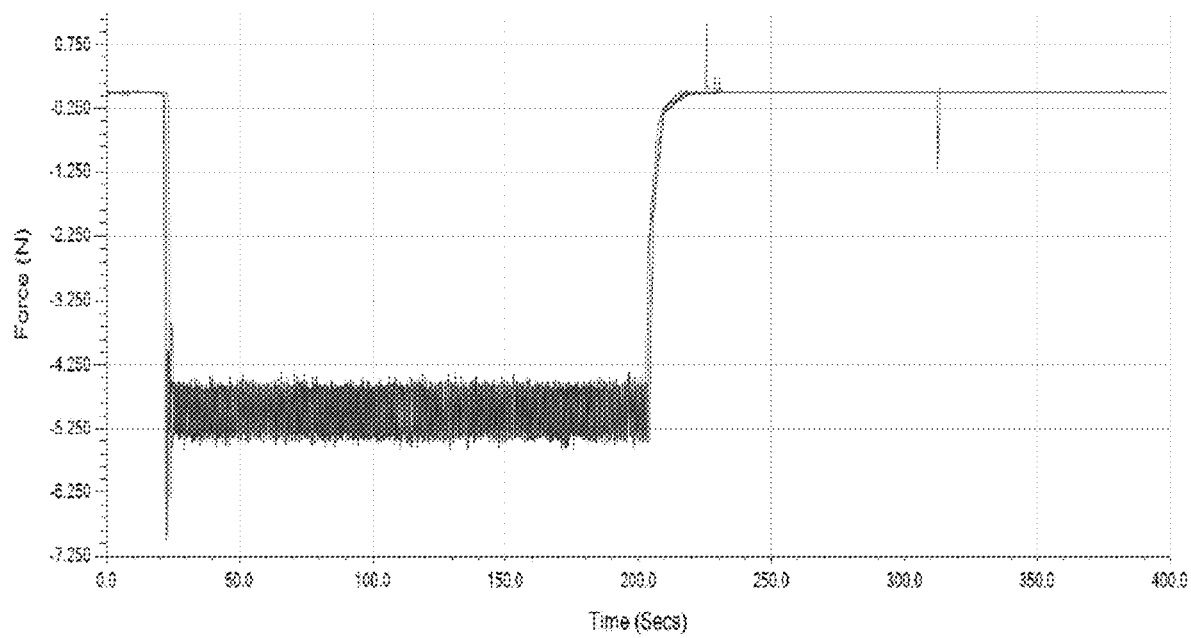
FIG. 3C
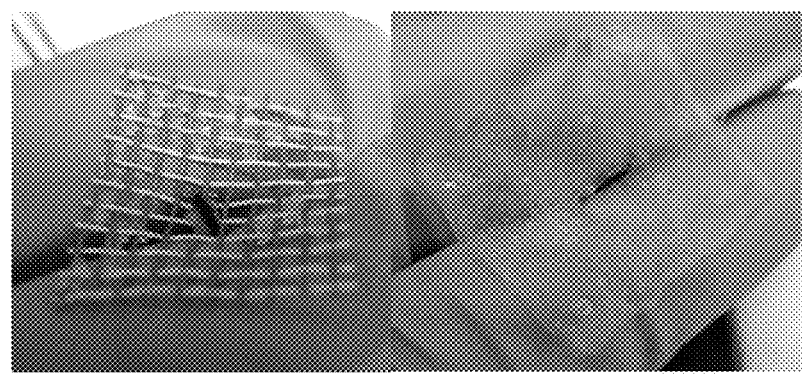
FIG. 4A
prior art
FIG. 4B

FIBRINOGEN-BASED TISSUE ADHESIVE PATCH

REFERENCE TO RELATED APPLICATIONS

This application is Continuation-in-Part of U.S. patent application Ser. No. 16/699,773, filed Dec. 2, 2019, which is a Continuation-in-Part of U.S. patent application Ser. No. 15/769,313, filed Apr. 18, 2018, now abandoned, which is a national phase filing of International (PCT) Pat. Appl. No. PCT/IL2016/051090, filed Oct. 6, 2016, and claims priority from U.S. Provisional Pat. Appl. No. 62/243,158, filed Oct. 19, 2015. All of these earlier applications are incorporated by reference in their entirety.

FIELD OF THE INVENTION

This invention relates in general to tissue sealant adhesive patches. In particular, it relates to an improved method for making tissue sealant adhesive patches.

BACKGROUND OF THE INVENTION

Wound dressings, tissue coatings, and tissue adhesives are examples of devices that serve to stop or prevent leakage of blood and other bodily fluids. These dressings can serve to seal open wounds, prevent infection, and so on. Many types of wound dressings and tissue adhesives known in the literature incorporate one or more coagulants such as fibrinogen.

Methods are known in the art for preparation of polymeric films suitable for medical use. For example, European Pat. Appl. No. 0334998 discloses a method for the preparation of a microporous membrane-like, polymeric film comprising: forming an aqueous phase having a viscosity of 0.07 to 0.5 Pa·s by use of a thickening agent soluble in water but not soluble in methylene chloride; emulsifying the aqueous phase in 5 to 15% methylene chloride solution having a viscosity of 0.1 to 1 Pa·s of a film forming thermoplastic polymer; spreading the polymer solution onto a support material to coat the support; volatizing the methylene chloride from the coated support; and removing the water.

Numerous examples are known in the literature of coagulant-containing tissue sealant compositions. U.S. Pat. No. 5,631,011 discloses a tissue treatment composition comprising fibrin or fibrinogen and a polymer that is biodegradable and biocompatible. The composition acts as a glue to bind tissue, e.g. a cut and sutured blood vessel. U.S. Pat. No. 6,699,844 discloses a fibrin-containing tissue sealant that also contains a derivative of hyaluronic acid. U.S. Pat. No. 6,162,241 discloses a hemostatic tissue sealant comprising a biocompatible, biodegradable hydrogel tissue sealant comprising crosslinkable groups having incorporated therein an effective amount of a hemostatic agent to stop the flow of blood from tissue in a medically acceptable period of time. U.S. Pat. No. 6,056,970 discloses compositions, produced by known paper-making technology, that comprise hemostatic compounds and bioabsorbable polymers.

Methods are also known in the art for preparing compositions that can release a pharmaceutically effective agent such as a hemostatic agent from a polymeric matrix. For example, European Pat. Appl. No. 1093824 discloses a biodegradable polymer such as a polylactide into which a dye is incorporated; the dye is released as the polymer degrades. PCT Pat. Appl. Pub. No. 99/21908 discloses compositions for delayed release of a pharmaceutical agent such as an anti-cancer drug, in which the pharmaceutical agent is incorporated into a biodegradable polymer that is injected into or applied onto tissue to be treated. Biodegradable polymers disclosed therein include inter alia A-B-A triblock copolymers in which the A block is a water-insoluble polymer (e.g. polycaprolactone or polycaprolactone—lactide copolymer) and the B block is a water-soluble polymer (e.g. polyethylene glycol). U.S. Pat. No. 6,194,005 discloses a method in which a powdered pharmaceutically effective agent is sprayed onto a warm lipid matrix, which thereby coats the agent. U.S. Pat. No. 6,579,537 discloses a method for producing inter alia a fibrinogen composition using a polyalkylene glycol. The basic method comprises producing a solution of fibrinogen and fibronectin and precipitating the fibrinogen and fibronectin by adding a polyalkylene glycol and an amino acid. U.S. Pat. Appl. Pub. No. 2012/0121532 discloses a method for preparing a dry and stable hemostatic composition. A dry hemostatic agent is mixed with a dry polymeric component in proportions such that on addition of an appropriate diluent (e.g. water), a polymeric matrix (e.g. a hydrogel) into which the hemostatic agent is incorporated.

Also known in the art are non-fibrous polymer films or coatings that incorporate a hemostatic agent such as thrombin. For example, U.S. Pat. Appl. Pub. No. 2007/0059346 discloses a film containing nitroglycerin and possibly other therapeutic agents; the film is made of a water-soluble polymer that can dissolve in the mouth of a patient.

Hemostatic wound dressings that incorporate fibrinogen are also known in the art. U.S. Pat. No. 7,189,410 discloses a layered fibrin sealant bandage comprising a backing layer and a hemostatic component layer containing fibrinogen, the fibrinogen acting to produce a clot when the bandage is applied to a wound. A family of patents that includes inter alia U.S. Pat. No. 6,054,122 discloses fibrin sealant bandages that comprise an occlusive backing, an adhesive layer on the wound-facing surface of the backing, and a layer of dry hemostatic materials (fibrinogen, thrombin, and $Ca^{2+}$ and/or Factor XIII as necessary). The dry materials adhere to, but are not incorporated into, the adhesive layer and are exposed at the time of use. U.S. Pat. Appl. Pub. No. 2006/0155235 discloses a hemostatic compression bandage that bandage comprises a flexible backing element, a powdered hemostatic substance, and a flexible film element. In this bandage, the hemostatic substance remains as a free powder. Immediately prior to use, the flexible film element is peeled away, exposing the powder, which is then placed directly on the wound. U.S. Pat. Appl. Pub. No. 2012/0070485 discloses a patch comprising a fibrin nanofiber mesh.

The present inventors have recently disclosed, in PCT Pat. Appl. Pub. No. WO2014/017509 (henceforth '509), which is hereby incorporated by reference in its entirety, fibrinogen-based tissue adhesive patches in which a fibrin sealant is incorporated into a polymer film. In contrast to those known in the art, the patches disclosed in '509 do not have any mesh or woven component, and use the fibrin sealant only to attach the patch to the tissue, the sealing of the tissue being performed by the polymer film. These patches thus provide a significant savings in material and ease of use.

Ideally, a tissue adhesive patch would remain intact long enough to stop bleeding or leakage of fluid from the tissue being sealed, but would decompose or degrade rapidly thereafter in order to minimize tissue irritation. The patches disclosed in '509 remain intact for more than two weeks, which is longer than necessary for some applications, in which a decomposition time on the order of days would be preferable. There is therefore a long-felt but as yet unmet need for an improved tissue adhesive patch that retains the advantages of the patches disclosed in '509, but that has a faster degradation time.

SUMMARY OF THE INVENTION

The tissue adhesive patches disclosed in the present invention are designed to meet this need. A tissue adhesive patch is disclosed that comprises a backing made of a biocompatible polymer, which acts to seal tissue into or out of which fluid is leaking, and a hemostatic agent (e.g. a fibrinogen sealant) incorporated into a surface of the backing. In preferred embodiments of the invention, the hemostatic agent acts to bind the backing to the tissue rather than to seal the tissue. The inventors have discovered that, surprisingly, the critical parameter that determines the half-life of the film is the ratio of the hydrophilic to hydrophobic components of the biocompatible polymers that make up the polymer film and that the degradation time of the patch is a sensitive function of this ratio. The invention herein disclosed additionally comprises methods of preparation and use of the tissue adhesive patch.

It is therefore an object of the present invention to disclose a fibrinogen-based tissue adhesive patch, wherein said adhesive patch comprises backing made from a film made of a biocompatible polyethylene glycol-caprolactone-lactide (PEG-CL-LA) triblock copolymer (PECALA) comprising PEG having a molecular weight of between 3000 and 3500 and a CL:LA ratio of 34:2; and a fibrinogen sealant comprising less than 8 mg/cm$^2$ fibrinogen and less than 20 IU/cm$^2$ thrombin incorporated into said biocompatible polymer backing. It is within the essence of the invention wherein said PECALA comprises PEG-CL-LA units connected by isocyanate linkages; said fibrinogen sealant is incorporated into a surface of said biocompatible polymer backing; and, said adhesive patch does not include any interpenetrating polymer network; any mesh or woven component; any non-woven fabric; or any material made by methods of paper-making technology.

In preferred embodiments of the invention, said fibrinogen sealant comprises about 2 mg/cm$^2$ fibrinogen and 10 IU/cm$^2$ thrombin. In more preferred embodiments of the invention, said fibrinogen sealant comprises less than 8 mg/cm$^2$ fibrinogen, less than 20 IU/cm$^2$ thrombin, and CaCl$_2$. In some preferred embodiments of the invention, said fibrinogen sealant consists of less than 8 mg/cm$^2$ fibrinogen, less than 20 IU/cm$^2$ thrombin, and CaCl$_2$. In some particularly preferred embodiments of the invention, said fibrinogen sealant consists of about 2 mg/cm$^2$ fibrinogen, about 10 IU/cm$^2$ thrombin, and CaCl$_2$.

In particularly preferred embodiments of the invention the fibrinogen sealant is incorporated into said backing such that said fibrinogen sealant remains partially exposed at said at least one surface. In some preferred embodiments of the invention, said adhesive patch does not include any interpenetrating polymer network. In some preferred embodiments of the invention, said adhesive patch does not include any mesh component. In some preferred embodiments of the invention, said adhesive patch does not include any woven component. In some preferred embodiments of the invention, said adhesive patch does not include any non-woven component. In some preferred embodiments of the invention, said adhesive patch does not include any woven fabric. In some preferred embodiments of the invention, said adhesive patch does not include any non-woven fabric. In some preferred embodiments of the invention, said adhesive patch does not include any material made by methods of paper-making technology.

It is a further object of this invention to disclose such a fibrinogen-based tissue adhesive patch, wherein said backing comprises a film made of a biocompatible polyurethane polymer comprising units of a biocompatible polymer connected by isocyanate linkages. In some preferred embodiments of the invention in which said backing comprises a film made of a biocompatible polyurethane polymer comprising units of a biocompatible polymer connected by isocyanate linkages, said polyurethane linkages are the product of reaction between two biocompatible polymer units and an aliphatic diisocyanate. In some particularly preferred embodiments of the invention, said aliphatic diisocyanate is hexamethylene diisocyanate (HDI).

It is a further object of this invention to disclose the fibrinogen-based tissue adhesive patch as defined in any of the above, wherein said PECALA comprises PEG having a molecular weight of between 3000 and 3500 and a CL:LA ratio of 34:2.

It is a further object of this invention to disclose the fibrinogen-based tissue adhesive patch as defined in any of the above, wherein at least one parameter characterizing said PECALA is fixed so as to provide said patch with a predetermined degradation time. In some embodiments of the invention, said at least one parameter is selected from the group consisting of: PEG molecular weight; ratio of hydrophilic to hydrophobic components; CL:LA ratio; and crystallinity. In some preferred embodiments of the invention, said predetermined degradation time is no more than two weeks. In some particularly preferred embodiments of the invention, said predetermined degradation time is between 10 and 14 days.

It is a further object of this invention to disclose a tissue adhesive patch as defined in any of the above, wherein said backing is characterized by at least one physical characteristic selected from the group consisting of: a Young's Modulus of between 50 MPa and 200 MPa; a tensile strength of between 5 MPa and 15 MPa; a melting point of between 45° C. and 52° C.; a water uptake of between 30% and 50%; and, a breakdown time in water (half-life) of between 15 days and 30 days.

It is a further object of this invention to disclose the fibrinogen-based tissue adhesive patch as defined in any of the above, wherein said patch is characterized by a thickness of about 200 μm. It is a further object of this invention to disclose such a tissue adhesive patch as defined in any of the above, wherein said backing is characterized by a thickness of about 100 μm.

It is a further object of this invention to disclose a tissue adhesive patch as defined in any of the above, wherein said patch is configured such that when said adhesive patch is in contact with a tissue, exposure of said adhesive patch to a fluid activates said fibrinogen sealant such that said fibrinogen sealant acts to attach said backing to said tissue.

It is a further object of this invention to disclose a tissue adhesive patch as defined in any of the above, wherein said fibrinogen sealant is incorporated into said at least one surface to a depth of between about 20 microns and about 60 microns.

It is a further object of this invention to disclose a tissue adhesive patch as defined in any of the above, wherein said fibrinogen sealant is not distributed throughout said backing.

It is a further object of this invention to disclose the fibrinogen-based tissue adhesive patch as defined in any of the above, wherein said fibrinogen sealant additionally comprises at least one additive. In some embodiments of the invention, said additive is selected from the group consisting of additives for extending the adhesion half-life of said film, pharmaceutically active agents, and analgesics. In some embodiments of the invention, said additive is a plasmin inhibitor for extending the adhesion half-life of said film. In some embodiments of the invention, said additive is a pharmaceutically active agent for targeted or controlled release.

It is a further object of this invention to disclose the fibrinogen-based tissue adhesive patch as defined in any of the above, wherein said sealant is incorporated into said polymer backing such that a force of 1.25-1.75 N/cm$^2$ is required to remove a sealant patch from tissue to which it has adhered.

It is a further object of this invention to disclose the fibrinogen-based tissue adhesive patch as defined in any of the above, wherein said polymer backing is characterized by an adhesive strength, and sealant is incorporated into said polymer backing such that said patch is characterized by a sealing ability that arises primarily from said adhesive strength of said polymer backing. In preferred embodiments of the invention, said patch is configured such that after said patch has been attached to a substrate and a detachment force is then applied to said patch, said patch undergoes adhesive failure along the interface between said sealant and said substrate.

It is a further object of this invention to disclose a method for producing a tissue adhesive patch, comprising: (a) casting a polymer film from a biocompatible polyurethane polymer selected from the group consisting of polyethylene glycol—polycaprolactone copolymers; polyethylene glycol—DL-lactide copolymers; and polyethylene glycol—polycaprolactone—DL-lactide copolymers, thereby creating a polymer film characterized by a thickness; (b) softening said polymer film; (c) placing a powdered tissue sealant material on a surface of said polymer film; and, (d) pressing said polymer film until at least a portion of said powdered tissue sealant material is at least partially incorporated into said surface of said polymer film; wherein said step of pressing said polymer film comprises pressing said polymer film until said powdered tissue sealant material is incorporated into said surface of said polymer film to a depth of between 20 μm and 60 μm.

It is a further object of this invention to disclose a method for producing a fibrinogen-based tissue adhesive patch, wherein said method comprises: casting a polymer film from PECALA, thereby creating a polymer film characterized by a thickness; softening said polymer film; placing a fibrinogen sealant comprising less than 8 mg/cm$^2$ fibrinogen and less than 20 IU/cm$^2$ thrombin on a surface of said polymer film; and, pressing said polymer film until at least a portion of said fibrinogen sealant is at least partially incorporated into said surface of said polymer film. In some preferred embodiments of the invention, said step of pressing said polymer film until at least a portion of said fibrinogen sealant is incorporated into a surface of said polymer film comprises pressing said polymer film until said fibrinogen sealant is incorporated into said at least one surface to a depth of between 20 μm and 60 μm.

It is a further object of this invention to disclose a method for preparing a tissue adhesive patch, comprising: (a) heating to a predetermined temperature a work surface in connection with a source of vacuum; (b) engaging said vacuum to said work surface; (c) applying to said work surface a solution of a biocompatible polyurethane polymer selected from the group consisting of polyethylene glycol—poly-caprolactone copolymers; polyethylene glycol—DL-lactide copolymers; and polyethylene glycol—polycaprolactone—DL-lactide copolymers; (d) adjusting a polymer blade to a predetermined height above said work surface; (e) spreading said solution of said biocompatible polyurethane polymer over said work surface with said polymer blade; (f) evaporating said solvent, thereby creating a non-permeable biocompatible polymer film characterized by a thickness; (g) heating said work surface above said softening temperature; (h) spreading powdered tissue sealant material over said polymer film; (i) placing over said polymer film a top release sheet over said powder and polymer film; (j) applying pressure to said top release sheet so as to at least partially incorporate said powdered tissue sealant material into a surface of said polymer film, thereby forming a film of adhesive patch material; (k) removing said top release sheet from said film of adhesive patch material; (l) releasing said vacuum; (m) cooling said work surface to room temperature; and, (n) removing said adhesive patch material from said work surface; wherein said step of applying pressure to said top release sheet comprises applying pressure to said top release sheet so as to incorporate said powdered sealant material into said surface of said polymer film to a depth of between 20 μm and 60 μm.

It is a further object of this invention to disclose a method for preparing a fibrinogen-based tissue adhesive patch, wherein said method comprises: heating to a predetermined temperature a work surface in connection with a source of vacuum; engaging said vacuum to said work surface; applying a solution of PECALA to said work surface; adjusting a polymer blade to a predetermined height above said work surface; spreading said solution of PECALA over said work surface with said polymer blade; evaporating said solvent, thereby creating a non-permeable biocompatible polymer film characterized by a thickness; heating said work surface above said softening temperature; spreading over said polymer film a powder comprising a fibrinogen sealant, said fibrinogen sealant comprising less than 8 mg/cm$^2$ fibrinogen and less than 20 IU/cm$^2$ thrombin; placing over said polymer film a top release sheet over said powder and polymer film; applying pressure to said top release sheet so as to at least partially incorporate said powder into a surface of said polymer film, thereby forming a film of adhesive patch material; removing said top release sheet from said film of adhesive patch material; releasing said vacuum; cooling said work surface to room temperature; and, removing said adhesive patch material from said work surface. In some preferred embodiments of the method, said step of applying pressure to said top release sheet comprises applying pressure to said top release sheet so as to incorporate said powder into a surface of said polymer film to a depth of between 20 μm and 60 μm.

It is a further object of this invention to disclose the method as defined in any of the above, wherein said biocompatible polymer is a polyethylene glycol—polycaprolactone—DL-lactide copolymer comprising polyethylene glycol having a molecular weight of between 3000 and 3500, a polycaprolactone to lactide ratio of 34:2, and polyethylene glycol—polycaprolactone—DL-lactide units connected by isocyanate linkages.

It is a further object of this invention to disclose the method as defined in any of the above, wherein said powdered tissue sealant material is selected from the group consisting of a fibrinogen sealant comprising less than 8 mg/cm$^2$ fibrinogen and less than 20 IU/cm$^2$ thrombin; and pig plasma proteins comprising fibrinogen and thrombin.

It is a further object of this invention to disclose the method as defined in any of the above, wherein said tissue sealant is a fibrinogen sealant comprising less than 8 mg/cm$^2$ fibrinogen, less than 20 IU/cm$^2$ thrombin, and $CaCl_2$.

It is a further object of this invention to disclose the method as defined in any of the above, wherein in embodiments that comprise a step of placing a powdered tissue sealant material on a surface of said polymer film, said step of placing a powdered tissue sealant material on a surface of said polymer film comprises placing 1-3 mg/cm$^2$ powdered tissue sealant material on said polymer film; and in embodiments that comprise a step of spreading powdered tissue sealant material over said polymer film, said step of spreading powdered tissue sealant material over said polymer film comprises spreading 1-3 mg/cm$^2$ powdered tissue sealant material over said polymer film.

It is a further object of this invention to disclose the method as defined in any of the above, wherein in embodiments that comprise a step of placing a powdered tissue sealant material on a surface of said polymer film, said step of placing a powdered tissue sealant material on a surface of said polymer film comprises placing a layer of powdered tissue sealant material characterized by a thickness of 30-70 µm on said polymer film; and in embodiments that comprise a step of spreading powdered tissue sealant material over said polymer film, said step of spreading powdered tissue sealant material over said polymer film comprises spreading a layer of powdered tissue sealant material characterized by a thickness of 30-70 µm over said polymer film.

It is a further object of this invention to disclose the method as defined in any of the above, wherein said step of casting a polymer film comprises casting a polymer film of thickness of about 200 µm. It is a further object of this invention to disclose the method as defined in any of the above, wherein said step of casting a polymer film comprises casting a polymer film of thickness of about 100 µm.

It is a further object of this invention to disclose the method as defined in any of the above, wherein said method does not include any step of distributing said fibrinogen sealant throughout said backing.

It is a further object of this invention to disclose a method of treating a leak of fluid into or out of a body part, comprising applying a tissue adhesive patch as defined in any of the above to said body part, thereby activating said fibrinogen sealant such that said fibrinogen sealant adheres said tissue adhesive patch to said body part, thereby sealing said body part. In some embodiments of the method, said body part is an artery or organ. In some embodiments of the invention, said leak of fluid is selected from the group consisting of arterial bleeding; organ tissue bleeding; bile anastomosis; cerebrospinal fluid leak; dura leak; and air leak in damaged lung tissue. In some embodiments of the method, said step of applying a tissue adhesive patch comprises manually pressing said patch on the surface of said body part.

It is a further object of this invention to disclose the use of a tissue adhesive patch as defined in any of the above in the treatment of a leak of fluid into or out of a body part. In some embodiments of the invention, the tissue adhesive patch as defined in any of the above is used in the treatment of a leak of fluid into or out of an artery or organ. In some embodiments of the invention, said leak of fluid is selected from the group consisting of arterial bleeding; organ tissue bleeding; bile anastomosis; cerebrospinal fluid leak; dura leak; and air leak in damaged lung tissue. In some preferred embodiments of the invention, said treatment comprises applying a tissue adhesive patch by manually pressing said patch on the surface of said body part.

It is a further object of this invention to disclose a method of treating a leak of fluid into or out of a body part, comprising applying a tissue adhesive patch prepared by the method as defined in any of the above to said body part such that contact with said fluid activates said fibrinogen sealant, causing said activated fibrinogen sealant to attach said polymer backing to said body part, thereby sealing said body part. In some embodiments of the method of treating a leak of fluid into or out of a body part, said body part is selected from the group consisting of arteries and organs. In some embodiments, said step of applying a tissue adhesive patch comprises manually pressing said patch on the surface of said body part.

BRIEF DESCRIPTION OF THE DRAWINGS

The invention will now be described with reference to the drawings, in which:

FIGS. 3A-3C present graphs showing results of measurements of the adhesive force of patches that comprise a polymer backing into which a fibrinogen-based sealant material is embedded in which the depth to which the sealant is embedded is varied;

FIGS. 4A and 4B contrast the failure modes of patches known in the art (FIG. 4A) with that of the patches of the present invention (FIG. 4B);

DETAILED DESCRIPTION OF THE PREFERRED EMBODIMENTS

Figure 1:
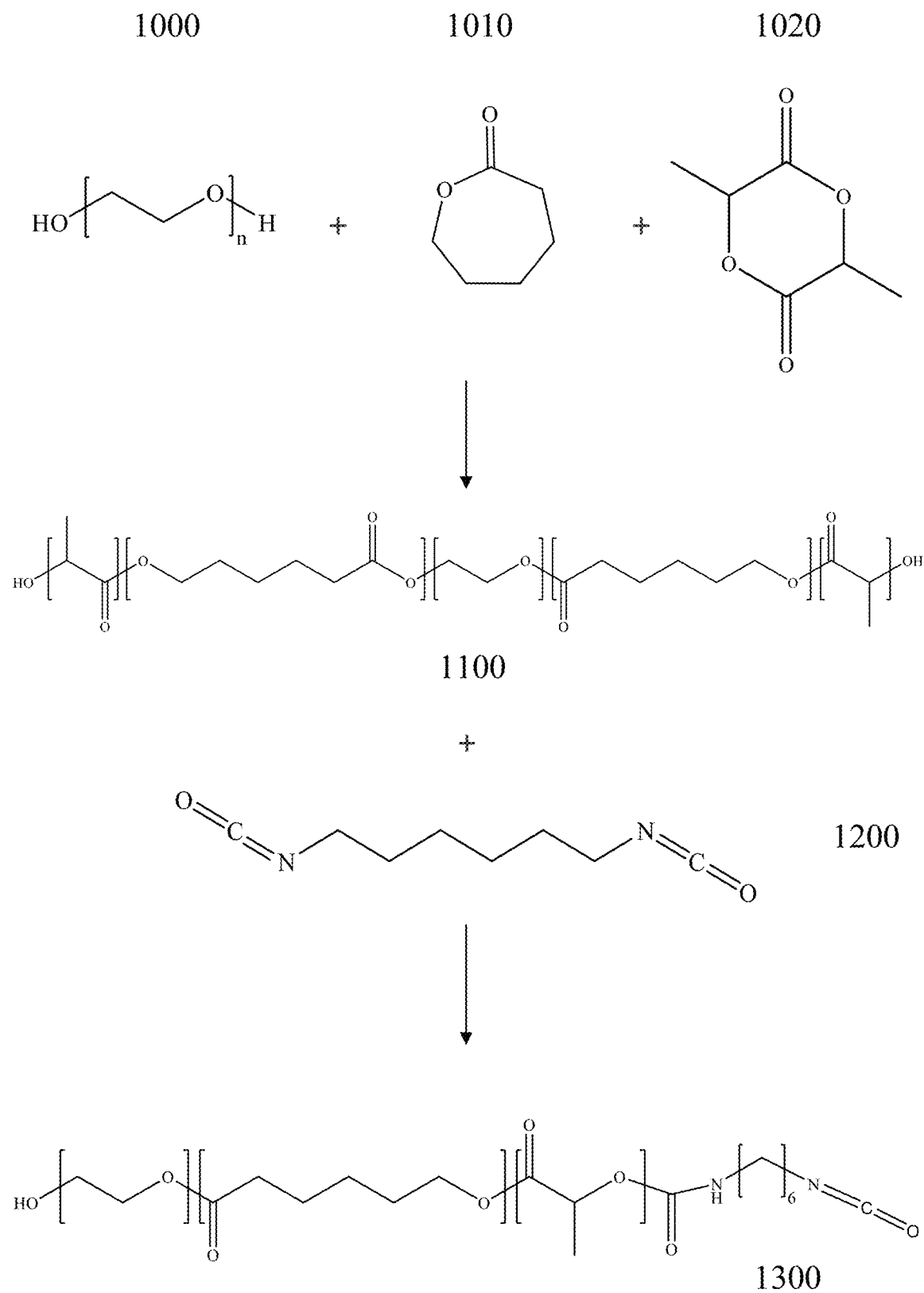
FIG. 1 presents a synthetic strategy for preparation of a PECALA biocompatible polyurethane polymer used as a backing in one exemplary non-limiting embodiment of the hemostatic patch herein disclosed.
Figure 2A:
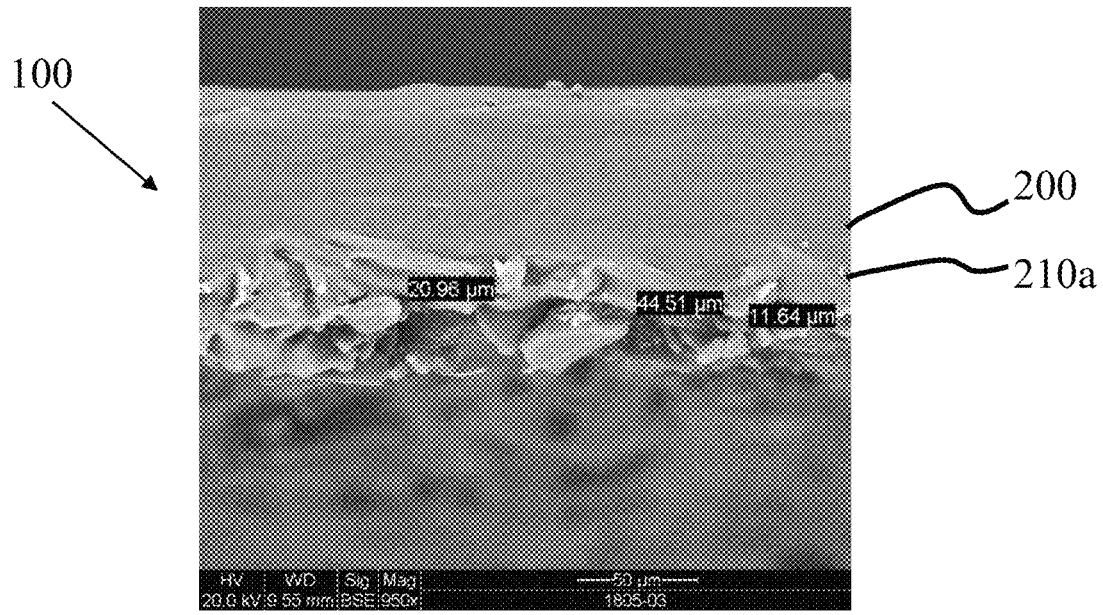
FIGS. 2A-2D are four SEM photographs that illustrate the incorporation of the fibrinogen sealant into the polymer backing in one non-limiting exemplary embodiment of the invention disclosed herein.
Figure 2B:
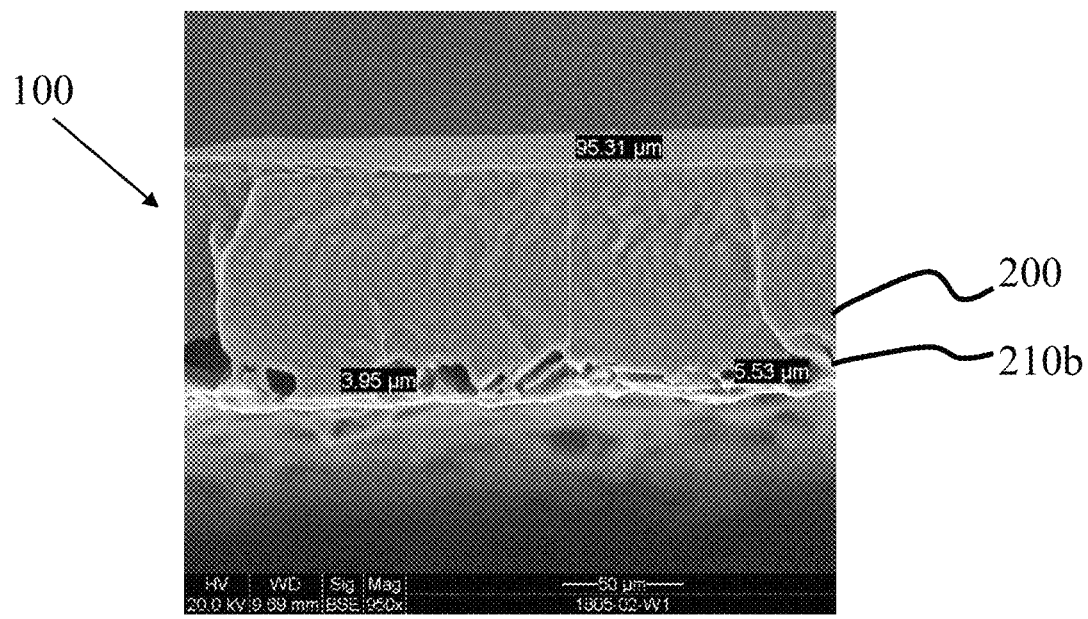
Figure 2C:
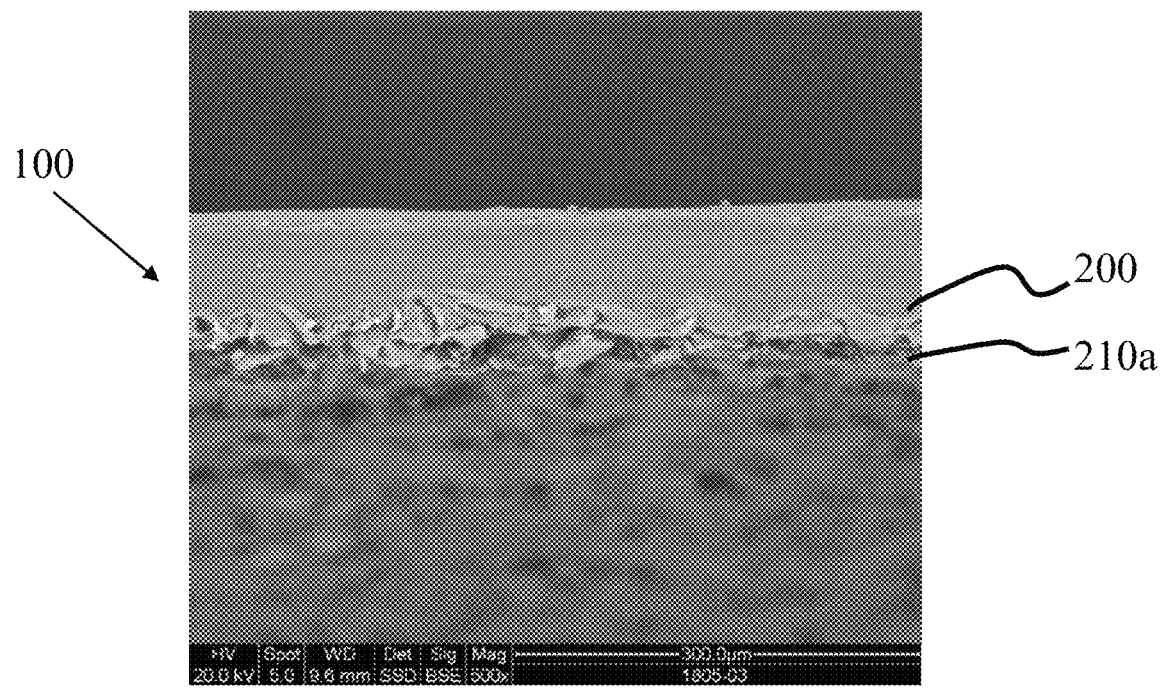
Figure 2D:
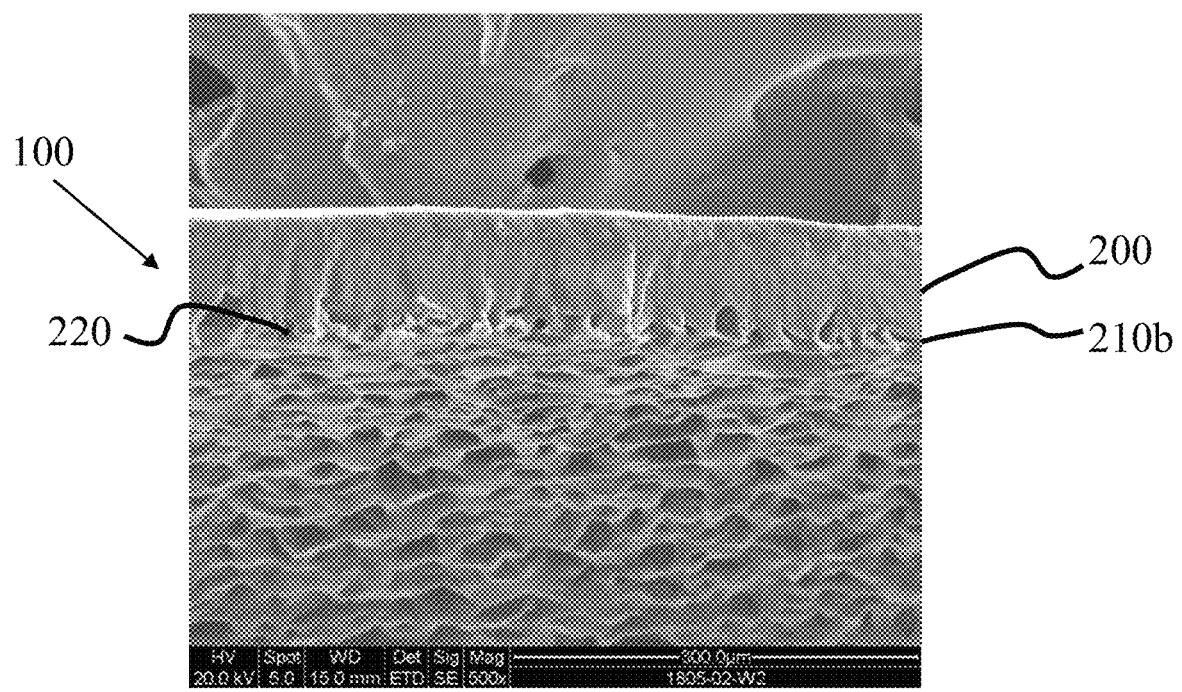

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore, the invention is not limited by that which is illustrated in the figures and described in the specification, but only as indicated in the accompanying claims, with the proper scope determined only by the broadest interpretation of said claims.

The following abbreviations are used throughout this application:

"PEG" is used to refer to polyethylene glycol.

"CL" is used to refer to caprolactone.

"LA" is used to refer to lactide, the cyclic diester of lactic acid.

As used herein, the term "PECALA" refers to a triblock copolymer comprising units comprising polyethylene glycol (PEG), caprolactone (CL), and lactide (LA) components. The individual PEG-CL-LA copolymer units may be connected by urethane linkages. When the term PECALA is followed by two numbers, the first indicates the ratio of hydrophilic (PEG) to hydrophobic (CL and LA) repeat units, and the second to the number of lactide units per triblock flank.

As used herein, the term "HDI" refers to hexamethylene diisocyanate (1,6-diisocyanatohexane, CAS number 822-06-0).

As used herein, the term "about," when applied to numerical quantities, refers to a range of ±25% of the nominal value.

As used herein, with reference to a polymer film or hemostatic patch attached to tissue, the terms "degrade" and "degradation" refer to the breakup of the polymer film or hemostatic patch into smaller pieces.

As used herein, with reference to the instant invention, when a particulate material is described as "incorporated" into a solid or semisolid material, unless stated otherwise, the term "incorporated" is used to refer to partial embedding in which the particles are partially within the solid or semisolid material and partially exposed above its surface.

In '509, the present inventors disclosed hemostatic patches that contain a fibrinogen component that acts solely to attach the polymer film to tissue and in which the polymer film rather than the fibrinogen component acts to seal the tissue. In contrast to hemostatic patches and dressings known in the art, in preferred embodiments, these patches do not include a mesh or woven component, woven or non-woven fabrics, or materials made by techniques known in paper-making technology. Rather, these patches comprise a single layer of polymer film into which fibrinogen and thrombin are incorporated, in contrast to multilayer hemostatic dressings known in the art (although embodiments in which additional layers are added for ease of handling or storage are not excluded from the scope of the present invention). Furthermore, the fibrinogen sealant component is physically incorporated into the polymer film to form a single integrated unit, in contrast to those hemostatic patches and dressings known in the art in which the coagulant is present as a free powder.

The patches disclosed in '509 generally retain their mechanical integrity for a period of several weeks following their attachment to the tissue. For some uses, however, the patch would ideally degrade on a faster time scale. For example, in the case of bleeding, the patch might not need to remain in place for more than a few days. Ideally, the patch would retain its mechanical integrity just long enough to complete the necessary treatment and would then degrade within a few days thereafter in order to minimize the possibility of negative interactions between the patch and the patient's body.

In order to assist a person of ordinary skill in the art to make and use the invention, and to assist in the understanding of the structure of the polymers used in preferred embodiments of the invention, reference is now made to FIG. 1, which shows a non-limiting exemplary synthetic strategy for preparation of PECALA, one polymer that the inventors have found is particularly useful for preparation of the hemostatic patches disclosed herein. In the first step, PEG (1000), ε-caprolactone (1010) and lactide (1020) are copolymerized to form macrodiol ester triblock copolymer 1100. Units of copolymer 1100 are then connected by reaction with diisocyanate 1200 to form the final polyurethane polymer product, PECALA (1300). In preferred embodiments of the invention, reaction with HDI (the diisocyanate shown in FIG. 1) is used to produce the polyurethane linkages, but any diisocyanate that will produce a biocompatible polymer with the desired physical properties such as tensile strength and breakdown time may be used.

The polymer used to produce the backing may be prepared by any method known in the art. It is emphasized that the foregoing description of the synthesis of PECALA is given solely in order that a person of ordinary skill in the art will understand the general structure of the polyurethane polymers preferably used in the invention. Any biocompatible polymer with the desired physical and chemical properties may be used in the patches of the invention herein disclosed, and any backing made with such biocompatible polymers is considered by the inventors to be within the scope of the invention regardless of the method used to synthesize the polymer. Furthermore, in preferred embodiments of the method of preparation of the hemostatic tissue adhesive patches described in detail below, the method does not include the synthesis of the polymer used as the backing, but rather begins with the casting of the polymer film. Thus, embodiments of the hemostatic patch, the method for making it, and the method for using it, in which the biocompatible polymer used as the backing is synthesized by another method, or obtained commercially, are considered by the inventors to be within the scope of the invention. Preparation methods of polymer backings made from other biocompatible polymers are described in detail in '509.

The thermoelastic polyurethane polymers used as backing material in preferred embodiments of the invention herein disclosed have ideal properties for their use as backing material for the hemostatic patch. Not only are they biocompatible and biodegradable with a relatively rapid breakdown time, they are characterized by high tensile strength, high toughness, and high elongation at break.

The present inventors have discovered, surprisingly, that for PECALA-based patches, several parameters can be varied in order to set a desired degradation time, and that patches with degradation times of on the order of two weeks can easily be produced. One important parameter is the ratio of the components of the triblock copolymer (e.g. the CL:LA ratio or ratio of hydrophobic to hydrophilic components). In general, the more CL units per PEG unit, the longer the degradation time, while the more CA units per PEG unit, the shorter degradation time (see the Example below). The degradation time is also apparently controlled by the crystallinity of the polymer; without wishing to be bound by theory, it appears that small amounts of LA prevent the CL from crystallizing, but too high a fraction of LA will itself crystallize, changing the degradation time. The molecular weight of the PEG used can also affect the degradation time. Thus, by proper control of the relative amounts of the components of the PECALA, it is possible to fine-tune the degradation time to the desired length.

Typical embodiments of the invention comprise a PECALA film comprising PEG of MW between 3000 and 3500 and a CL:LA ratio of 34:2 (i.e. 4 LA units and 68 CL units per PEG) into which a fibrinogen sealant comprising fibrinogen (≤8 mg/cm$^2$, preferably about 2 mg/cm$^2$) and thrombin (≤20 IU/cm$^2$, preferably about 10 mg/cm$^2$) has been incorporated. In preferred embodiments, the fibrinogen sealant also comprises $CaCl_2$. It may also include additives such as additives for extending the adhesion half-life of said film, pharmaceutically active agents, and analgesics.

The patch thickness is typically on the order of 100-200 μm. In preferred embodiments, the patches are about an order of magnitude thinner (typically 130-170 nm).

The patches may be prepared according to any method known in the art. For example, they can be prepared by a method based on the one disclosed in '509. In this method, a PECALA film is cast on a surface such as a glass slide from a solution of PECALA in a volatile organic solvent. The film is then heated to its softening point, and a powdered tissue sealant material is sprinkled onto the surface of the softened polymer film. In typical embodiments, the tissue sealant mixture has been micronized to a particle size of 25-75 nm. The inventors have found that this particle size is effective for a variety of tissue sealant materials, non-limiting examples of which include fibrinogen-based sealant materials, and pig plasma proteins. The sealant material is then pressed into the surface to a depth of 20-60 μm of the softened polymer film and allowed to cool to room temperature. The film is then optionally placed in a freezer (typically at about −20° C.) to aid in removing it from the surface on which it was prepared. Excess powder is removed from the patch by shaking and the patch then removed from the surface on which it was prepared.

The inventors have recently developed a second embodiment of the process for manufacture of the patches. This method uses a specially modified drawdown coater, and comprises: (a) heating to a predetermined temperature a work surface in connection with a source of vacuum; (b) engaging said vacuum to said work surface; (c) applying a solution to said work surface, said solution comprising a biocompatible polymer characterized by a softening temperature dissolved in a solvent; (d) adjusting a polymer blade to a predetermined height above said work surface; (e) spreading said solution over said work surface with said polymer blade; (f) evaporating said solvent, thereby creating a non-permeable biocompatible polymer film; (g) heating said work surface above said softening temperature; (h) spreading a powder comprising a tissue sealant over said polymer film; (i) placing over said polymer film a top release sheet over said powder and polymer film; (j) applying pressure to said top release sheet so as to at least partially incorporate said powder into said polymer film to a depth of 20-60 μm, thereby forming a film of adhesive patch material; (k) removing said top release sheet from said film of adhesive patch material; (l) releasing said vacuum; (m) cooling said work surface to room temperature; and, (n) removing said adhesive patch material from said work surface. Non-limiting examples of tissue sealant powders that can be used in this method include those listed above for the preceding embodiment of the invention.

Reference is now made to FIG. 2, which presents SEM photographs of one non-limiting embodiment of the hemostatic patch disclosed herein. FIG. 2A illustrates a cross-sectional view of a patch 100 of the instant invention. The patch includes a backing layer 200 that comprises PECALA film and has, in the example shown, a thickness of approximately 90-100 μm, and a layer of fibrin-containing sealant (210a). As can be seen in the photograph, the fibrin sealant layer extends into the PECALA film to a depth on the order of tens of microns, with no free powder remaining on the surface and no sealant present within the film beyond this surface layer. FIG. 2B illustrates a patch after the fibrin-containing sealant has been activated by contact with fluid. As can be seen in the figure, the fibrin-containing sealant has dissolved to leave a layer (210b) approximately 5 μm thick, and "craters" (220) in the polymer film. FIGS. 2C and 2D present similar views but at approximately half the magnification. The "craters" left behind after activation of the fibrin-containing sealant are more clearly visible at this magnification (see FIG. 2D).

The inventors have made the surprising discovery that the depth to which the tissue sealant powder is embedded into the backing layer in the polymeric film is critical. On the one hand, it is essential that the powder be embedded to a depth sufficient to enable it to remain attached to the film backing after the material has been activated (e.g. after activation of fibrinogen by thrombin) while being at least partially exposed to the tissue to which the patch is applied. On the other hand, in order for the invention to operate as described above, the tissue sealant powder must not fully penetrate the ~100 μm-thick polymeric backing layer. Embedding the sealant to a depth of 20-60 μm ensures that both of these conditions are met. To the best of the inventors' knowledge, the criticality of this parameter was unknown prior to their development of the invention disclosed herein.

In order to demonstrate the criticality of the depth to which the tissue sealant powder is embedded, the inventors performed a series of experiments in which a tissue sealant powder comprising fibrinogen and thrombin was embedded in a PECALA backing to varying depths, and the adhesive strength of the resulting tissue patch was measured according to the method disclosed in PCT Pat. Appl. Pub. No. WO2019/180713, which is hereby incorporated by reference in its entirety. This method measures the adhesive force by placing two patches on facing surfaces with the side that would normally contact the tissue exposed. Liquid is placed on one of the patches to activate the hemostatic agent, the patches are held together long enough so that they adhere to one another, and then the force necessary to detach them is measured.

Figure 3A:
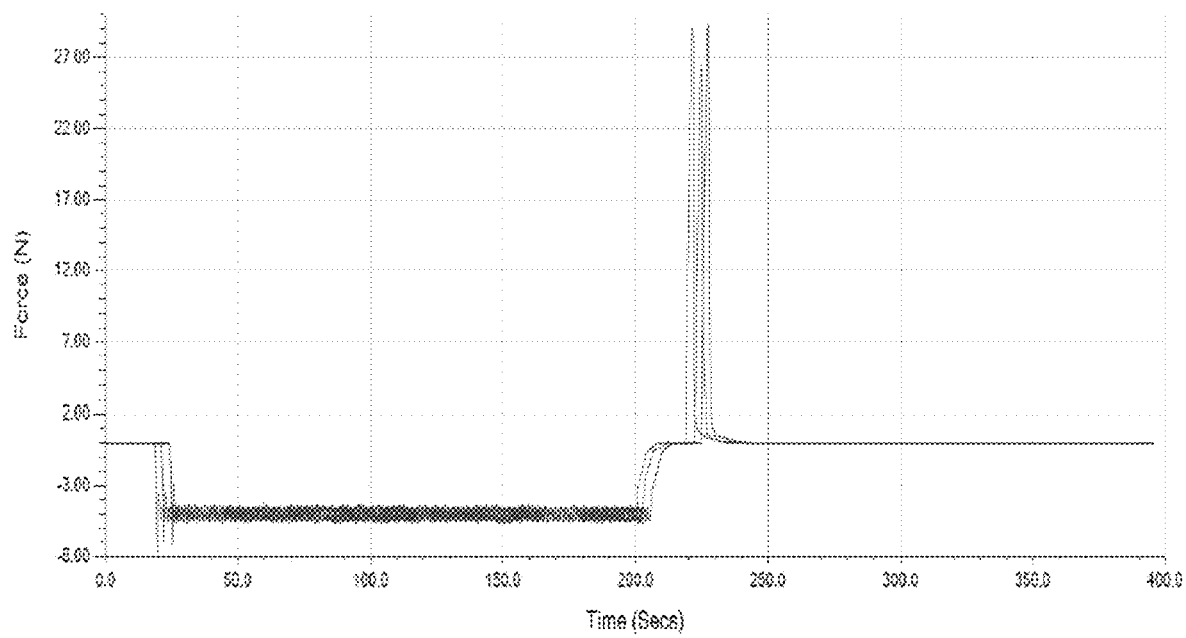
Figure 3B:
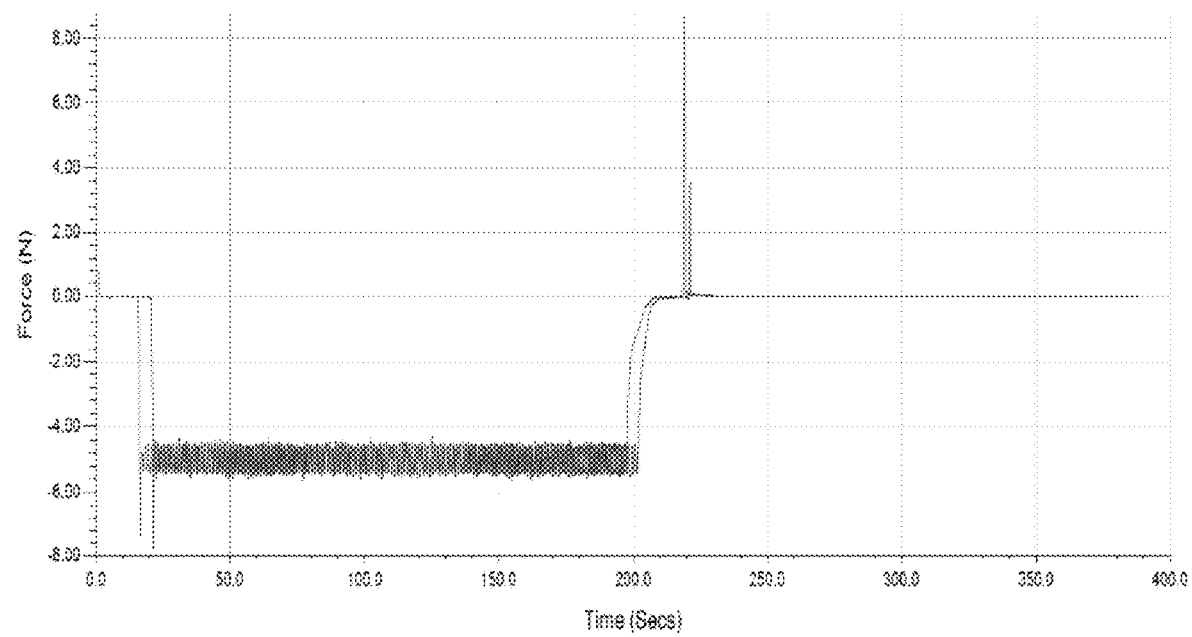

Reference is now made to FIG. 3, which presents a series of graphs showing the results of measurements of the adhesive strength of patches in which the fibrinogen sealant powder was embedded in the PECALA backing to a depth of 20-60 μm (FIG. 3A), <20 μm (FIG. 3B), or >60 μm (FIG. 3C). Each graph shows results for three independent measurements. The patches in which the sealant was embedded to a depth of 20-60 μm had an adhesive force of about 30 N. In contrast, the patches in which the sealant was embedded to <20 μm had an adhesive force of about 5 N, while those in which the sealant was embedded to a depth of >60 μm have an adhesive force of about 0.5 N. These results clearly demonstrate that a patch in which the sealant is embedded to a depth of 20-60 μm has an adhesive strength that is significantly higher than a similar patch in which the sealant is embedded to a depth outside of this range. To the best of our knowledge, the prior art does not provide any indication that the depth to which the powdered sealant material is embedded is a critical parameter that affects a primary physical property of interest or that the depth to which the sealant is embedded must be considered in the construction of a tissue sealant patch.

The configuration of the patches disclosed herein, namely, incorporation of a sealant material into the surface of a non-permeable polymer film backing, enables the tissue adhesive of the present invention to be used in a variety of unique applications. Non-limiting examples of applications in which the present invention can be used include covering traumatic and chronic wounds, stopping of arterial bleeding, stopping organ tissue bleeding, and sealing of other body fluids, for example, in treatment of bile anastomosis, cerebrospinal fluid and dura leaks, etc. In typical uses of the patch, it is applied to tissue from which fluid is leaking. Contact with fluid (particularly the fluid that is leaking) activates the fibrinogen sealant, thereby attaching the patch to the affected tissue. The polymer film then seals the leak without any necessity for application of further pressure. The patch then degrades without any necessity for further intervention over a time determined primarily by its composition, as described above. In typical embodiments of the invention, the patch degrades over a period of 10-14 days.

In typical embodiments of the patch, a force of about 5-7 N is required in order to detach a 2 cm×2 cm patch from tissue, corresponding to a detachment force of about 1.25-1.75 N/cm². Reference is now made to FIG. 4, which illustrates the failure mode of the patches of the present invention. FIG. 4A illustrates a mesh embedded with fibrin of a type known in the art. When a detachment force is applied, the mesh is detached from the tissue and only residues of fibrin remain on the mesh, with no evidence of tissue fragments seen on the mesh. This behavior indicates that hemostatic patches known in the art undergo cohesive failure, i.e. the adhesive itself loses its structural integrity, fragments, and breaks.

In contrast, as shown in FIG. 4B, when a detachment force is applied to the patches of the present invention, the film detaches with fragments of tissue remaining on the film, indicating that the tissue itself rather than the adhesive underwent mechanical failure. That is, in contrast to hemostatic patches known in the art, the patches of the present invention undergo adhesive failure along the interface between the adhesive and the substrate. Thus, the instant invention comprises patches in which the main contribution to the sealing ability arises from the adhesive strength of the polymer film rather than the rather weak internal strength of fibrin.

Figure 5:
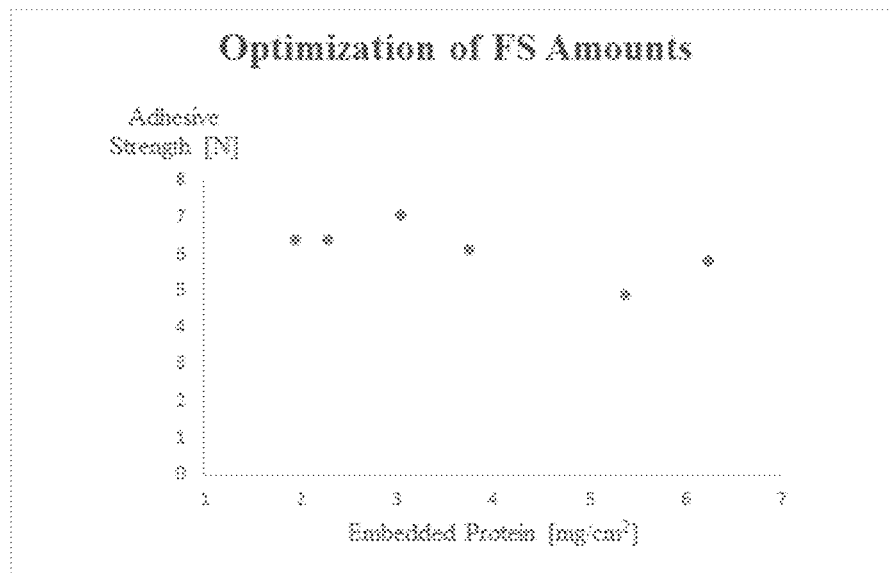
FIG. 5 presents a graph illustrating the adhesive strength of the patches of the present invention as a function of concentration of fibrin sealant; and, FIG. 6 presents a graph illustrating the degradation times of patches of the present invention made with different formulations of the polymer film.

Reference is now made to FIG. 5, which presents a graph showing the adhesive strength of the patches of the present invention as a function of the concentration of fibrin sealant. As can be seen from the figure, the adhesive strength is essentially independent of the amount of fibrin present. Thus, the patches of the present invention are effective with significantly less fibrin sealant than is used in patches known in the art. In preferred embodiments of the present invention, the fibrin sealant comprises about 2 mg/cm² fibrin and 10 IU/cm² thrombin.

While the above description has presented non-limiting embodiments of the invention in which the sealant comprises fibrinogen, patches in which other powdered tissue sealants are used are considered by the inventors to be within the scope of the invention. In some non-limiting embodiments, the sealant comprises powdered pig plasma protein. The inventors have found that the patches are effective when the sealant powder particles are of similar size to the particles of the fibrinogen/thrombin powder described above, and when the sealant is incorporated into the backing to a depth of 20-60 µm. Thus, in some preferred embodiments of the invention in which a sealant other than fibrinogen/thrombin is used, the powder comprises particles of sizes in the range of 25-75 nm. In some preferred embodiments of the invention in which a sealant other than fibrinogen/thrombin is used, the patches are prepared by placing 1-3 mg/cm² of sealant on the polymer backing prior to the incorporation of the sealant powder onto the backing. In some preferred embodiments of the invention in which a sealant other than fibrinogen/thrombin is used, the patches are prepared by placing a layer of powdered sealant having a thickness of 30-70 µm on top of the polymer backing prior to the step of incorporation of the sealant powder into the backing.

The following example illustrates certain non-limiting embodiments of the present invention in order to assist one of ordinary skill in the art to make and use the invention, and are not intended to be limiting in any way.

EXAMPLE

Figure 6:
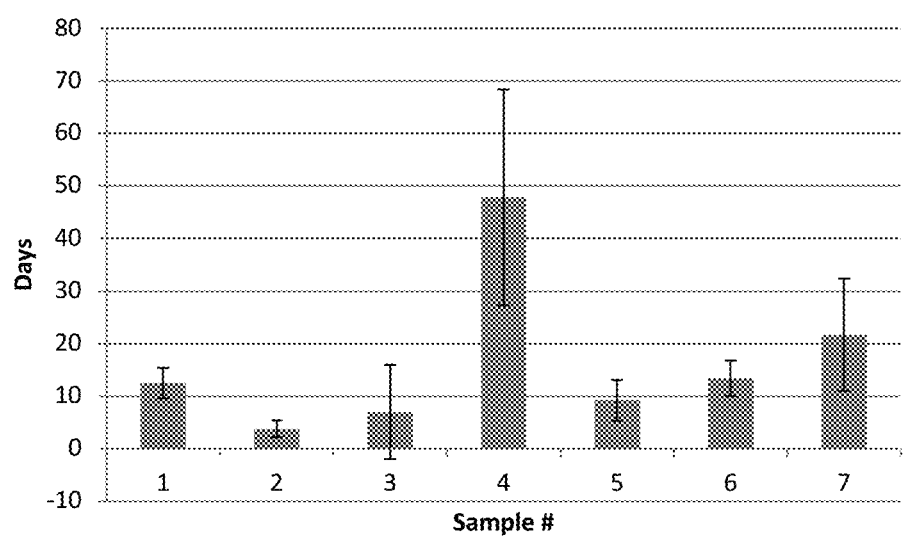

A series of hemostatic patches of the present invention were prepared with different PECALA formulations. The PECALA was prepared according to standard literature procedures. The degradation time of the patches was measured for a minimum of five independent samples. The results of the experiments are summarized in Table 1, and illustrated graphically in FIG. 6.

TABLE 1

| Sample | PEG MW | CL:LA ratio | Mean degradation time (days) |
|---|---|---|---|
| 1 | 3350 | 34:2 | 12.5 |
| 2 | 3350 | 44:3 | 3.8 |
| 3 | 3350 | 44:4 | 7.0 |
| 4 | 3350 | 34:1 | 47.8 |
| 5 | 6000 | 34:2 | 9.2 |
| 6 | 3000 | 34:2 | 13.4 |
| 7 | 3350 | 40:2 | 21.7 |

In the table, the CL:LA ratio is given relative to the number of PEG units; that is, a CL:LA ratio of n:m indicates that for each PEG unit in the polymer, there were 2n CL units and 2m LA units.

As can be seen from the table, in general, the degradation time tended to decrease with increasing PEG molecular weight, decreasing CL:LA ratio, increasing number of CL units per PEG unit, and decreasing number of LA units per PEG unit. Because the degradation time appears to be a function of polymer crystallinity as well, these general rules are only valid within limits; for example, increasing the number of CL units per LA unit will increase the crystallinity of the polymer.

The invention claimed is:

1. A method for producing a tissue adhesive patch, comprising:
   casting a polymer film from a biocompatible polyurethane polymer selected from the group consisting of polyethylene glycol—polycaprolactone copolymers; polyethylene glycol—DL-lactide copolymers; and polyethylene glycol—polycaprolactone—DL-lactide copolymers, thereby creating a polymer film characterized by a thickness;
   softening said polymer film;
   placing a powdered tissue sealant material on a surface of said polymer film; and,
   pressing said polymer film until at least a portion of said powdered tissue sealant material is at least partially incorporated into said surface of said polymer film;
   wherein:
   said step of pressing said polymer film comprises pressing said polymer film until said powdered tissue sealant material is incorporated into said surface of said polymer film to a depth of between 20 µm and 60 µm.

2. The method according to claim 1, wherein said biocompatible polymer is a polyethylene glycol—polycaprolactone—DL-lactide copolymer comprising polyethylene glycol having a molecular weight of between 3000 and 3500, a polycaprolactone to lactide ratio of 34:2, and polyethylene glycol—polycaprolactone—DL-lactide units connected by isocyanate linkages.

3. The method according to claim 1, wherein said powdered tissue sealant material is selected from the group consisting of a fibrinogen sealant comprising less than 8 mg/cm² fibrinogen and less than 20 IU/cm² thrombin; and pig plasma proteins comprising fibrinogen and thrombin.

4. The method according to claim 3, wherein said powdered tissue sealant material is a fibrinogen sealant comprising less than 8 mg/cm² fibrinogen, less than 20 IU/cm² thrombin, and CaCl₂).

5. The method according to claim 1, wherein said thickness is about 200 μm.

6. The method according to claim 1, wherein said step of placing a powdered tissue sealant material on a surface of said polymer film comprises placing 1-3 mg/cm$^2$ powdered tissue sealant material on said polymer film.

7. The method according to claim 1, wherein said step of placing a powdered tissue sealant material on a surface of said polymer film comprises placing a layer of powdered tissue sealant material characterized by a thickness of 30-70 μm on said polymer film.

8. The method according to claim 1, wherein said step of casting a polymer film from a biocompatible polyurethane polymer comprises casting a polymer film from a polyethylene glycol—polycaprolactone—DL-lactide copolymer.

* * * * *